United States Patent [19]

McGalliard et al.

[11] 4,185,978
[45] Jan. 29, 1980

[54] METHOD FOR CRYOGENIC SEPARATION OF CARBON DIOXIDE FROM HYDROCARBONS

[75] Inventors: Russell L. McGalliard, Chicago; Gary W. Larrabee, Hazel Crest, both of Ill.

[73] Assignee: Standard Oil Company (Indiana), Chicago, Ill.

[21] Appl. No.: 773,359

[22] Filed: Mar. 1, 1977

[51] Int. Cl.² .............................................. F25J 3/02
[52] U.S. Cl. .......................................... 62/28; 62/38; 62/23
[58] Field of Search .............................. 62/23, 28, 38

[56] References Cited

U.S. PATENT DOCUMENTS

| | | | |
|---|---|---|---|
| 3,397,138 | 8/1968 | Bacon | 62/38 |
| 3,595,782 | 7/1971 | Bucklin et al. | 62/38 |
| 4,012,212 | 3/1977 | Kniel | 62/28 |

*Primary Examiner*—Norman Yudkoff
*Attorney, Agent, or Firm*—Robert B. Stevenson; Arthur McIlroy

[57] ABSTRACT

The operation of a demethanizer being used to cryogenically separate high carbon dioxide content hydrocarbon feed into liquid ethane essentially free of both methane and carbon dioxide with simultaneous production of overhead gas comprising methane and carbon dioxide without carbon dioxide icing to foul equipment by virtue of maintaining pressure at which non-gaseous carbon dioxide remains dissolved in liquid hydrocarbon, can be improved by intentionally injecting a dehydrated methane-rich stripping gas to the bottom of the demethanizer. At temperatures below about −80° F., the addition of a stream such as dehydrated inlet gas stabilizes the demethanizer operation by making the carbon dioxide to ethane ratio of the liquid bottoms product less sensitive to temperature fluctuations in the reboiler system heating the bottoms. In this manner, product recovery is increased while acceptable carbon dioxide as well as methane content can be maintained. Such a method is compatible with closed-loop control of the reboiler temperature based on gas chromatography measurements.

5 Claims, 2 Drawing Figures

METHOD FOR CRYOGENIC SEPARATION OF CARBON DIOXIDE FROM HYDROCARBONS

BACKGROUND OF THE INVENTION

1. Field of the Invention

The present invention relates to an improved process for cryogenic separation of hydrocarbons in the presence of a relatively high carbon dioxide content wherein the hydrocarbon/carbon dioxide feed gas after precooling and turboexpansion is directed to a demethanizer column for the purpose of separating a methane/carbon dioxide overhead from an ethane-containing liquid hydrocarbon bottoms. More specifically, it is concerned with improving and stabilizing the operation of the demethanizer column by intentionally injecting a dehydrated methane-containing stripping gas to the bottom of the demethanizer.

2. Description of the Prior Art

High carbon dioxide content feed gases such as may be encountered in certain fields of the United States which may range in carbon dioxide content between 0.1 and 15% by volume continue to be a problem to the extent that cryogenic handling procedures may cause separation from the feed gas of carbon dioxide as "ice" with destructive effect on equipment and efficiency. Traditionally, carbon dioxide has been separated in advance of processing for hydrocarbon product separation with an added step such as amine treating, molecular sieve adsorption, methanol absorption or caustic treating or not removed, see for example U.S. Pat. No. 3,292,380 to Bucklin. In cases where the carbon dioxide is not removed from the feed gas, it must be removed from the product ethane by one of the above-mentioned sweetening processes.

In U.S. Pat. No. 3,595,782 to Bucklin et al., a method for producing an ethane-containing liquid hydrocarbon essentially free of both methane and carbon dioxide without carbon dioxide icing to foul equipment is disclosed. The process involves passing an expanded precooled feed gas through a demethanizer separation column at a temperature below −80° F. and pressure consistent with maintaining the non-gaseous carbon dioxide dissolved in an ethane-containing liquid hydrocarbon phase. Thus, carbon dioxide icing does not occur and an ethane output substantially free of carbon dioxide; e.g., less than 0.1% carbon dioxide content, can be achieved. However, in operating such a plant on a commercial scale, the carbon dioxide content in the product is extremely sensitive to the reboiler temperature at the bottom of the demethanizer. For example, in one commercial scale plant, it was observed that at design level a one-degree change in the reboiler temperature would result in rapid temperature drops in selected tray temperatures and an increase in carbon dioxide content in the product from essentially zero to a value that exceeded the specification limit. Under such circumstances, closed-loop control of the reboiler temperature based on gas chromatograph carbon dioxide to ethane ratio measurements and the like is not possible.

SUMMARY OF THE INVENTION

In view of the criticality of controlling the reboiler temperature at the base of a cryogenic demethanizer, we have discovered an improved method of operating the demethanizer such that the separation process is stabilized and desensitized with respect to reboiler temperature fluctuations. The improvement involves injecting an appropriate stream of gas with, preferably, a methane content greater than that in the reboiler vapors into the bottom of the demethanizer. The dehydrated hydrocarbon feed gas being processed in plant is an acceptable source of stripping gas. The rate of injection is maintained such that the bottoms product methane content remains sufficiently low to meet commercial standards (usually about 0.1 to 1.0 liquid volume percent).

Thus, a primary objective of this invention is to provide a method for producing an ethane and heavier hydrocarbon product having a low carbon dioxide and methane content from gas having objectionable amounts of carbon dioxide in a cryogenic demethanizer in a manner such that the quantity and quality of ethane being produced will not be compromised because of minor temperature excursions which occur at the bottom of the demethanizer column.

Accordingly, this invention provides in a method of treating high pressure hydrocarbon feed gas having relatively high carbon dioxide content to produce a liquid ethane-containing hydrocarbon product substantially free of carbon dioxide and a gaseous product comprising of methane and carbon dioxide including the steps of (a) expanding a precooled gaseous portion of said hydrocarbon feed gas through a turbine to produce a mixture of gaseous hydrocarbon including methane and liquid hydrocarbon including liquid ethane, said mixture being at a temperature below −80° F., (b) passing said mixture to a demethanizer separation column at a temperature below −80° F., and (c) separating said mixture in said demethanizer such that essentially all the methane and gaseous carbon dioxide is recovered overhead as said gaseous product and essentially all said liquid hydrocarbon including liquid ethane is recovered at the bottom of said demethanizer as said liquid ethane-containing hydrocarbon product, while maintaining non-gaseous carbon dioxide dissolved in said liquid ethane-containing hydrocarbon in said turbine and demethanizer, the specific improvement comprising; injecting into said ethane-containing hydrocarbon at the bottom of said demethanizer separation column an effective amount of a dehydrated methane-containing sweep gas such as to stabilize and desensitize the separation process occurring within said demethanizer with respect to temperature variations of said liquid bottoms.

DESCRIPTION OF THE PREFERRED EMBODIMENTS

The improved method for operating the cryogenic demethanizer such as to achieve greater stability and lower sensitivity to reboiler temperature can perhaps best be described and understood by reference to the accompanying drawing.

Figure 1:
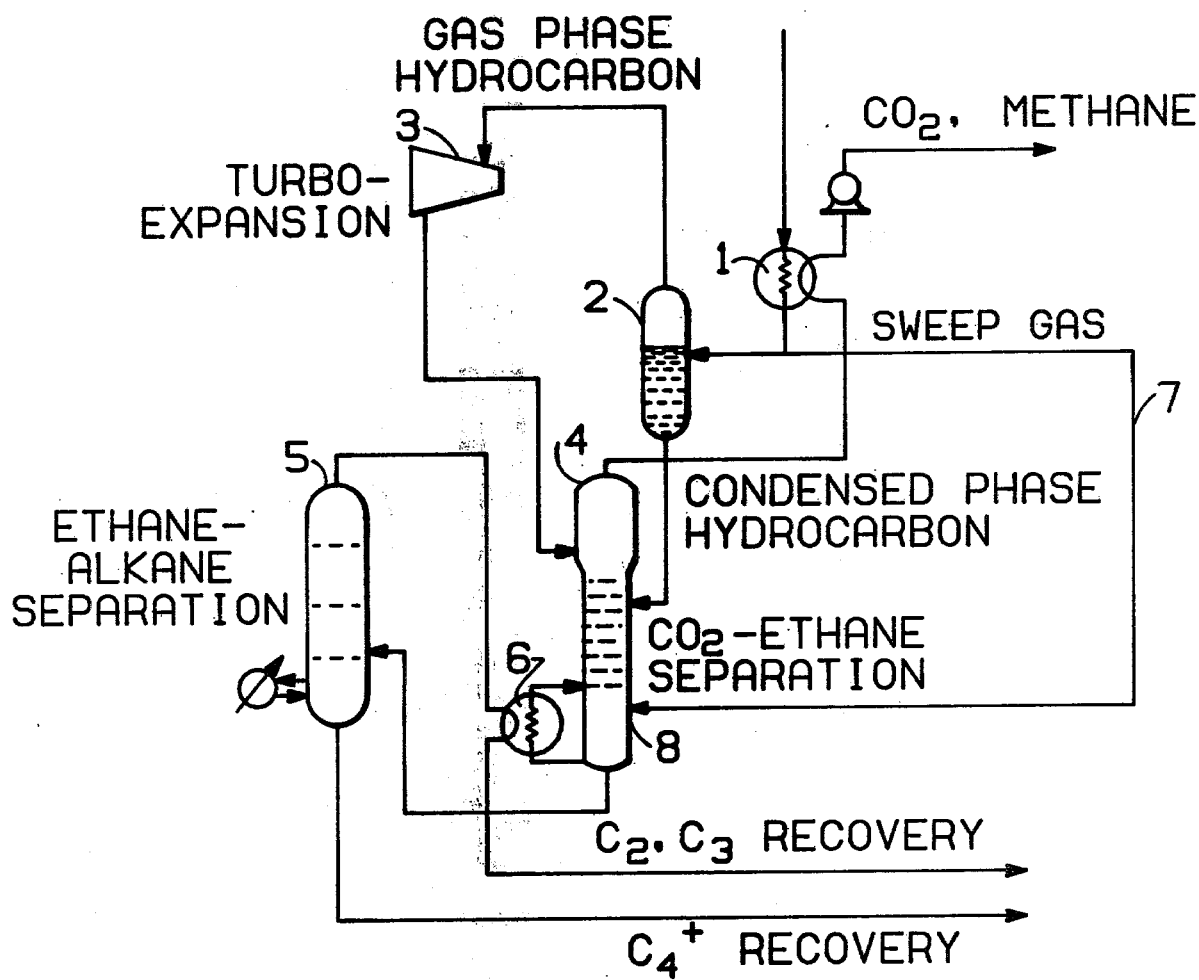
FIG. 1 of the drawing is a flow diagram of a specific cryogenic method of separating carbon dioxide from hydrocarbons which is known in the prior art and is presented here to illustrate the basic modification required to perform the improvement which is the subject of this invention.

FIG. 1 of the drawing is a simplified flow diagram of a specific cryogenic method of separating carbon dioxide from hydrocarbons as already known in the art. It is presented here to illustrate conceptually how the modifications involved in this invention fits into the overall flow diagram of a typical commercial embodiment. Briefly, the known process involves passing dehydrated high pressure hydrocarbon feed containing carbon dioxide through a heat exchanger 1 to precool the feed. The resulting liquid and gas mixture is then separated in tank 2. The gas phase from this separation is sent through a turbine expander 3 before entering the top of the demethanizer column 4. The condensed phase from this separation is injected midway down the demethanizer column. The conditions within the demethanizer are maintained below −80° F. and at an appropriate pressure such that essentially all of the methane and carbon dioxide are separated and withdrawn overhead while any non-gaseous carbon dioxide remains in solution with the liquid ethane and higher molecular weight hydrocarbons being withdrawn from the bottom. The bottoms then undergo further fractionation in a separate distillation column 5 with ethane and propane being removed overhead and then used to supply heat to the reboiler heat exchanger 6 at the bottom of the demethanizer. The butane and heavier cut is recovered at the bottom of the second distillation column to complete the process. As previously stated, this process is basically known in the art and the purpose of presenting FIG. 1 is to show how the present improvement is incorporated into a known specific embodiment. Dashed line 7 which delivers a portion of the dehydrated feed gas to the demethanizer and injects it as a sweep gas at point 8 is illustrative of the basic improvement of our invention. For a more detailed description of the known process, less this improvement, see U.S. Pat. No. 3,595,782 here incorporated by reference.

Figure 2:
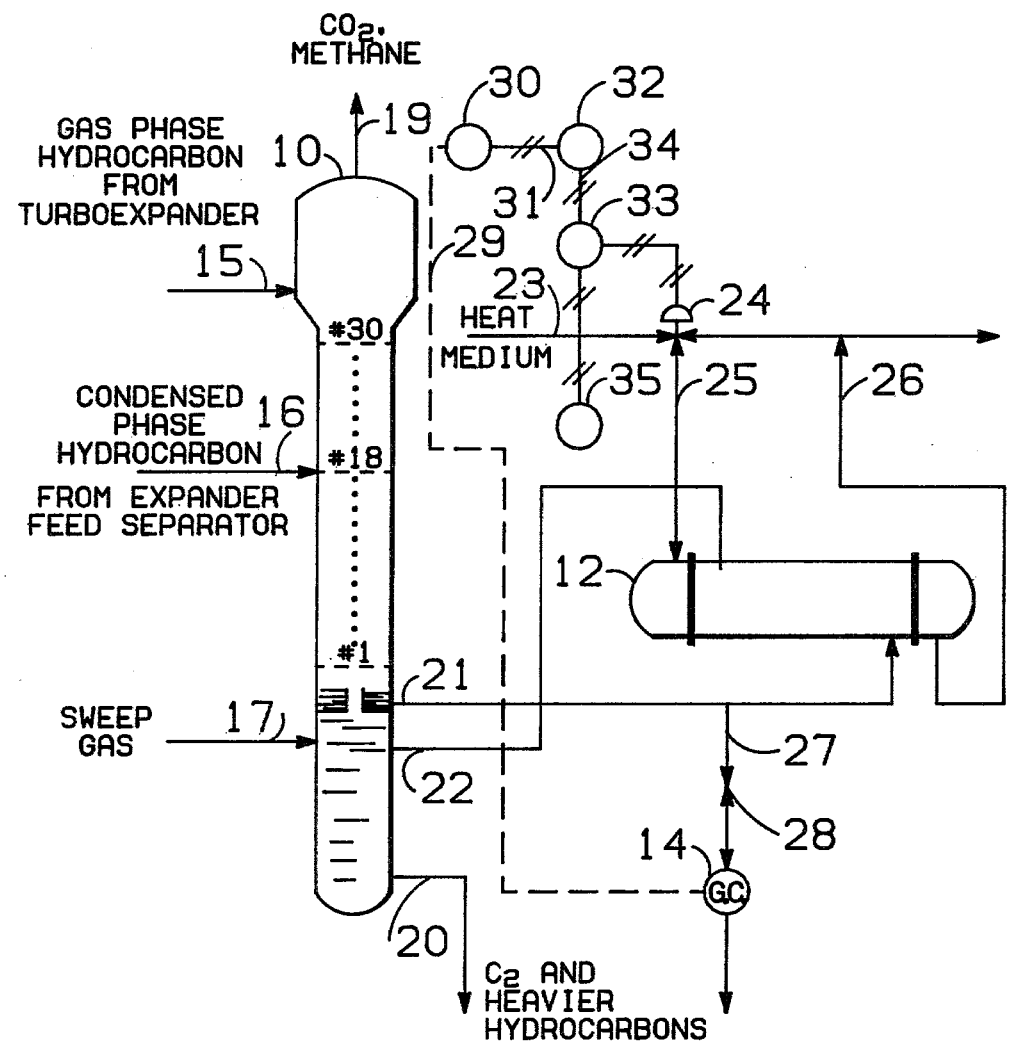
FIG. 2 of the drawing is a flow diagram illustrating the improved process of this invention is more detailed terms than FIG. 1 including an associated closed-loop chromatographic control scheme.

In FIG. 2 the details of a typical commercial scale 30-tray demethanizer 10 being operated according to the present invention is illustrated along with a reboiler 12 and an associated gas chromatograph 14 for control of the bottom reheat temperature. The gas phase hydrocarbon passing through the turboexpander (not shown) enters the demethanizer 10 via line 15 at the top while the condensed phase from the expander feed separator (not shown) enters midway to tray #18 through line 16. A portion of the original dehydrated hydrocarbon feed gas contaminated with carbon dioxide is intentionally added to the bottom of the demethanizer 10 through line 17 as a sweep gas which admittedly enriches the entire column and to a certain degree the liquid ethane-containing bottoms with gases which in principle are to be cryogenically distilled overhead. It is this intentional addition of a purge gas at the bottom of the demethanizer which forms the basis of our invention and serves to distinguish the present improved process from that which has been practiced in the past.

Two product streams are recovered from demethanizer 10. A methane and carbon dioxide mixture is removed overhead via line 19 and a liquid ethane-containing hydrocarbon product stream is withdrawn from the bottom through line 20. In order to control the bottom temperature by supplying the proper amount of heat to the bottom of the demethanizer 10, demethanizer liquids are removed via line 21 and sent through reboiler heat exchanger 12. The temperature controlled liquid and vapor stream is then returned to the demethanizer through line 22. Heat energy is supplied to the reboiler 12 from an external heat medium circulating in line 23. The heat medium enters the reboiler 12 via control valve 24 and line 25. After passing through the reboiler, it returns to line 23 via line 26.

Automation of the reboiler temperature control is achieved by removal of a sample of the demethanizer liquid from line 21. This sample is sent via line 27 and valve 28 to gas chromatograph 14 wherein the carbon dioxide to ethane ratio is measured. The difference between this measured value and a predetermined setpoint value characteristic of the desired product composition is transmitted in the form of an electrical signal through dashed line 29 to a current to pneumatic converter 30. A corresponding pneumatic signal is then transmitted via line 31 to a temperature reset controller 32. Controller 32 responds by reassigning a new temperature range to temperature controller 33 via line 34. Controller 33 then brings the temperature of the fluid in line 22 being monitored by temperature transmitter 35 back into agreement with the new reset temperature range by repositioning the valve 24. In this manner, the amount of jacket water, the heat medium, flowing through the reboiler is controlled such as to maintain the desired temperature of the reboiler effluent being returned to the bottom of the demethanizer and this temperature is reset automatically according to the measured concentration of carbon dioxide present in the liquid bottoms relative to a desired product specification limit.

The significance and practical advantage of practicing our improved cryogenic separation method can perhaps best be demonstrated by considering the details of a typical commercial scale plant being operated according to the preferred embodiments illustrated in FIG. 1 and FIG. 2 with and without the injection of the dehydrated sweep gas. For example, a 30-tray demethanizer having a tray efficiency of 50 percent (15 theoretical trays) and an expander efficiency of 70 percent when operated according to FIG. 1 without sweep gas injection at a design flow rate of 40 MMSCF (million standard cubic feet per day) of a feed gas having the composition set out in the following Table I at a demethanizer pressure of 250 psia and reboiler effluent controlled bottom temperature of 48.2° F. would be expected to produce an overhead methane/carbon dioxide residue gas having a gross heating value in excess of 1000 BTU/SCF and produce a liquid bottoms product stream having less than 0.75 volume percent carbon dioxide with ethane and propane recoveries of 58.7 and 95.4 percent, respectively.

TABLE I

| INLET GAS ANALYSIS | |
|---|---|
| Component | Mol Percent |
| Nitrogen | 0.30 |
| Carbon Dioxide | 0.45 |
| Methane | 93.32 |
| Ethane | 3.99 |
| Propane | 1.27 |
| i-Butane | 0.14 |
| n-Butane | 0.26 |
| i-Pentane | 0.08 |
| n-Pentane | 0.06 |
| Hexanes Plus | 0.13 |
| | 100.00 |

Such a plant, when operated at design recovery levels, exhibited extreme sensitivity to reboiler temperature in that a one-degree change in reboiler temperature caused certain tray temperatures to drop rapidly and caused the carbon dioxide content in the liquid product to increase from a zero gas chromatographic measured value to a value exceeding acceptable product specification. In this particular case, closed-loop gas chromatographic control of reboiler temperature was for all practical purposes inoperative.

The magnitude of the instability induced by a one-degree change in the above example can be illustrated by considering tray 6. At a reboiler temperature of 49° F., the temperature of tray 6 is 16° F. At 48° F. the temperature falls to −43° F., a change of 59° F. The large tray temperature change is caused by correspondingly large carbon dioxide and ethane concentration changes. Lowering the reboiler temperature from 49° F. to 48° F. will create an anticipated change of the carbon dioxide content in the liquid of tray 6 from 2.4 to b 37 mole percent and in the vapor from 6.9 to 62.8 mol percent. Simultaneously, the ethane content of tray 6 in the liquid decreases from 77.3 to 41.2 mol percent and in the vapor from 85.1 to 20.6 mol percent. Obviously, when a large increase in the concentration of the more volatile component occurs, a drastic drop in the equilibrium temperature will be observed. It is this tremendous reboiler temperature sensitivity and associated separation column instability that is alleviated by the use of an appropriate purge stream injection at the bottom of the demethanizer.

Injecting stripping gas in the bottom of the demethanizer has a positive effect on product recovery and tower controllability. Table II below, summarizes the recovery levels for three cases, the first without stripping gas and the second and third with 750 thousand standard cubic feet per day of dehydrated feed gas being injected.

TABLE II

| Case | Stripping Gas Rate MSCFD | Reboiler Temp. °F. | Recovery % Ethane | Recovery % Propane | Reboiler Duty MMBTU/HR |
|---|---|---|---|---|---|
| 1 | 0 | 48.2 | 58.7 | 95.4 | 1.495 |
| 2 | 750 | 48.2 | 49.2 | 94.7 | 1.465 |
| 3 | 750 | 40.7 | 60.3 | 95.7 | 1.331 |

In each case the demethanizer pressure is 250 psia, and in Case 1 and Case 3 the product meets carbon dioxide concentration specification. Case 3 showed the highest ethane and propane recovery. Injecting stripping gas also increases recovery by allowing retention of methane in the product. A purchaser will customarily pay for methane in the product up to some contractually specified limit, e.g., 0.75 volume percent. Case 3 relative to Case 1 takes greater advantage of this factor in the sense that liquid product presently sells at about ten times the price of the methane/carbon dioxide residue gas. But, most important, Case 3 is compatible with gas chromatographic closed-loop control of the reboiler temperature without severe demethanizer instability.

An effective amount of sweep gas for purposes of this invention refers to sweep gas flow rates that range from about one-fortieth up to about one-fourth of the flow rate of the feed gas being processed. In principle, this sweep gas can be any gas which is inert and does not liquefy under the operation conditions. Since the sweep gas dilutes the demethanizer overheat stream, it is preferable to use a methane-containing sweep gas. The rate of injecting the methane-containing sweep gas has been successfully tested from as low as 120 MCFD to as high as 750 MCFD in the above example. However, other rates would be acceptable and for purposes of this invention should be considered equivalent. The pragmatic consideration of methane content tolerable in the final product should in principle be the primary factor in determining an upper limit. Thus, the specific rate will vary from plant to plant, and will also vary with feed gas composition and operating conditions.

A liquid ethane-containing hydrocarbon product, substantially free of carbon dioxide for purposes of this invention, is referring to carbon dioxide concentrations of about 1.0 to 3.0 liquid volume percent or less, and preferably 0.1 liquid volume percent. Having thus described the preferred commercial scale embodiment, it should be apparent that the basic invention can be employed with other types of analytical monitors than gas chromatography, other known flow and temperature control systems as well as other chemically similar purge systems without departing from the intended scope of the claims.

We claim:

1. In a method of treating hydrocarbon feed gas having relatively high carbon dioxide content to produce a liquid ethane-containing hydrocarbon product substantially free of carbon dioxide and a gaseous product comprised of methane and carbon dioxide wherein said treating includes:

(a) expanding a precooled gaseous portion of said hydrocarbon feed gas through a turbine to produce a mixture of gaseous hydrocarbon, including methane, and liquid hydrocarbon, including liquid ethane, said mixture being at a temperature below −80° F.;

(b) passing said mixture to a demethanizer separation column at a temperature below −80° F.; and (c) separating said mixture in said demethanizer such that essentially all the methane and gaseous carbon dioxide are recovered overhead as said gaseous product and essentially all said liquid hydrocarbon, including liquid ethane, is recovered at the bottom of said demethanizer as said liquid ethane-containing hydrocarbon product, while maintaining non-gaseous carbon dioxide dissolved in said liquid ethane-containing hydrocarbon in said turbine and demethanizer, the specific improvement comprising;

injecting from outside the demethanizer column into said ethane-containing liquid hydrocarbon at the bottom of said demethanizer separation column an effective amount of an inert sweep gas which does not liquefy under operating conditions such as to stabilize and desensitize the separation process occurring within said demethanizer with respect to temperature variations of said liquid hydrocarbon at the bottom of said column.

2. A method of claim 1 wherein said sweep gas is a dehydrated methane-containing gas.

3. A method of claim 2 wherein said dehydrated methane-containing sweep gas is taken from said hydrocarbon feed gas.

4. A method of claim 3 wherein said dehydrated methane-containing sweep gas is from about one-fortieth to about one-fourth of said hydrocarbon feed gas.

5. A method of claim 3 wherein said hydrocarbon feed gas is being processed at about 40 MMSCFD at about 250 psia, with the addition of from about 120 to about 750 MSCFD of said sweep gas.

* * * * *